US00PP37462P2

(12) United States Plant Patent
McBee et al.

(10) Patent No.: US PP37,462 P2
(45) Date of Patent: Jun. 9, 2026

(54) ***DIERVILLA* PLANT NAMED 'Baildierone'**

(50) Latin Name: ***Diervilla* X *splendens***
Varietal Denomination: Baildierone

(71) Applicant: Bailey Nurseries, Newport, MN (US)

(72) Inventors: Oren McBee, Bishop, GA (US); David Jonathan Roberts, Athens, GA (US); Justin Schulze, Athens, GA (US)

(73) Assignee: BAILEY NURSERIES, INC., Newport, MN (US)

( * ) Notice: Subject to any disclaimer, the term of this patent is extended or adjusted under 35 U.S.C. 154(b) by 0 days.

(21) Appl. No.: 19/366,139

(22) Filed: Oct. 22, 2025

(51) Int. Cl.
*A01H 5/12* (2018.01)
*A01H 6/00* (2018.01)

(52) U.S. Cl.
USPC ..... Plt./226

(58) Field of Classification Search
USPC ..... Plt./226
CPC ... A01H 5/12; A01H 5/00; A01H 5/02; A01H 6/00
See application file for complete search history.

(56) References Cited

U.S. PATENT DOCUMENTS

PP34,138 P2 * 4/2022 Mathey ..... Plt./226

* cited by examiner

*Primary Examiner* — June Hwu
(74) *Attorney, Agent, or Firm* — Penny J. Aguirre

(57) ABSTRACT

A new cultivar of *Diervilla* named 'Baildierone' that is characterized by its foliage with new growth that is orange in color and changes to yellow and chartreuse, its foliage that is resistant to sun bleaching, its minimal spreading by suckering, and its cold hardiness in U.S.D.A. Zone 3.

4 Drawing Sheets

Botanical classification: *Diervilla* X *splendens*.
Variety denomination: 'Baildierone'.

BACKGROUND OF THE INVENTION

The present invention relates to a new and distinct cultivar of *Diervilla* X *splendens* and will be referred to hereafter by its cultivar name, 'Baildierone'. 'Baildierone' is a new cultivar of bush honeysuckle grown for use as a landscape plant.

The new cultivar is the result of a controlled breeding program conducted by the Inventors in Watkinsville, Georgia. The goal of the breeding program was to develop a new cultivar of *Diervilla* with reduced suckering and yellow foliage that is resistant to sun scorch.

The Inventors made a cross in summer of 2018 between *Diervilla* cultivars 'Diwibru01' (U.S. Plant Pat. No. 27,932) as the female parent and 'El Madrigal' (U.S. Plant Pat. No. 28,060) as the male parent. The Inventors selected 'Baildierone' in summer of 2019 as a single unique plant amongst the seedlings that resulted from the above cross.

Asexual propagation of the new cultivar was first accomplished by one of the Inventors using softwood stem cuttings in summer of 2019 in Winterville, Georgia. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Baildierone' as a unique cultivar of *Diervilla*.

1. 'Baildierone' exhibits foliage with new growth that is orange in color and changes to yellow and chartreuse.
2. 'Baildierone' exhibits foliage that is resistant to sun bleaching.
3. 'Baildierone' exhibits minimal spreading by suckering.
4. 'Baildierone' exhibits cold hardiness in U.S.D.A. Zone 3.

The female parent plant of 'Baildierone' differs from 'Baildierone' in having foliage that lacks orange coloration on the new growth and that is prone to sun bleaching. The male parent differs from 'Baildierone' in having purple to bronze-green foliage and a plant habit that is more compact and with more suckering. 'Baildierone' can be most closely compared to *Diervilla* cultivars 'Bocofire' (U.S. Plant Pat. No. 33,978), and 'SMNDSS' (U.S. Plant Pat. No. 34,138). 'Bocofire' is similar to 'Baildierone' in having new foliage that emerges orange tinged and changes to yellow and in blooming in June and repeat blooming in late summer. 'Bocofire' differs from 'Baildierone' in having new growth that is darker orange and more red in color, a later first flowering flush, and a smaller plant size. 'SMNDSS' is similar to 'Baildierone' in having a similar plant size and growth habit. 'SMNDSS' differs from 'Baildierone' in having new foliage growth that is darker red-orange in color and persists longer and then fades to light green.

BRIEF DESCRIPTION OF THE DRAWINGS

The accompanying colored photographs illustrate the overall appearance and distinct characteristics of the new *Diervilla*. The photographs in FIG. 1, FIG. 2, and FIG. 3 were taken of 2-year-old plants of the new cultivar as grown outdoors in 2-gallon container in Newport, Minnesota. The photograph in FIG. 4 was taken of 5-year-old plants of the new cultivar as grown outdoors in a trial field in Newport, Minnesota.

The photograph in FIG. 1 illustrates the overall appearance of 'Baildierone'.

Figure 1:
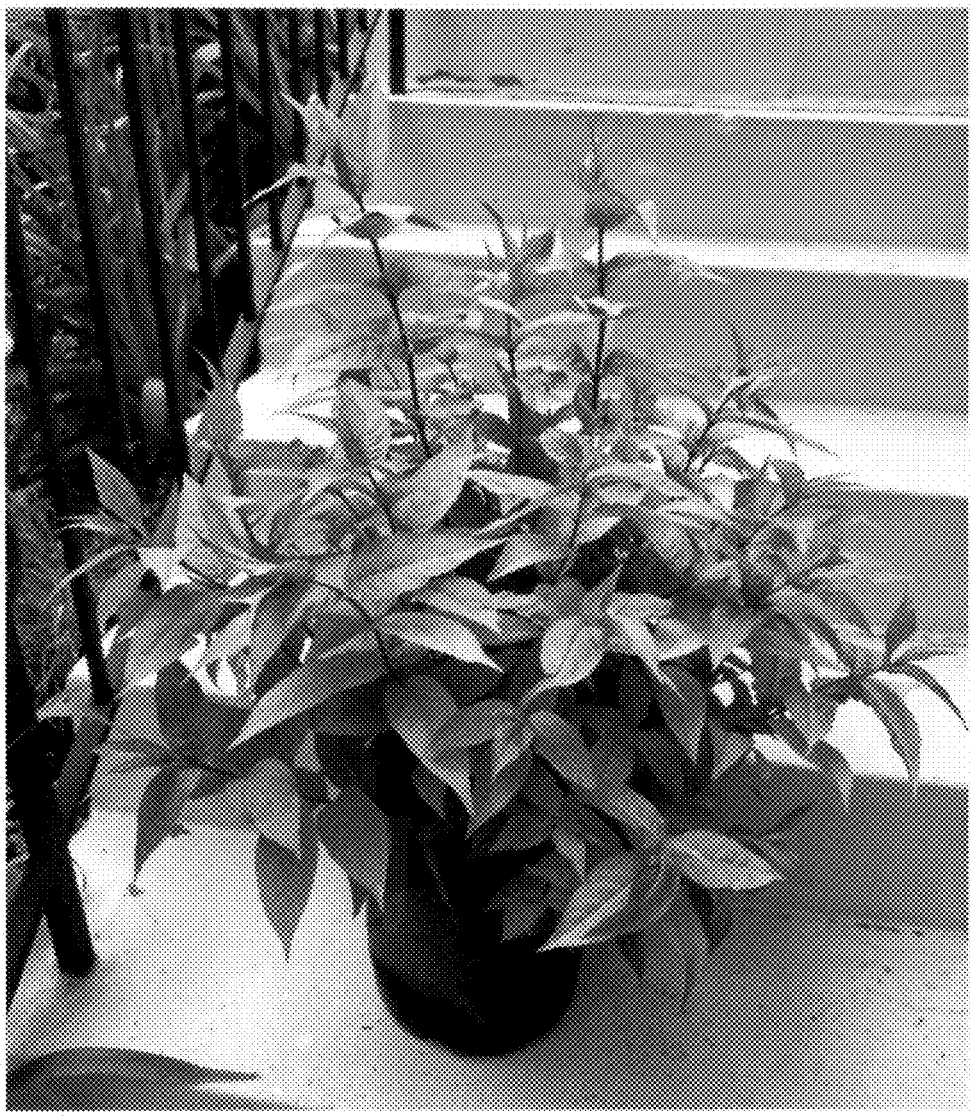
Figure 2:
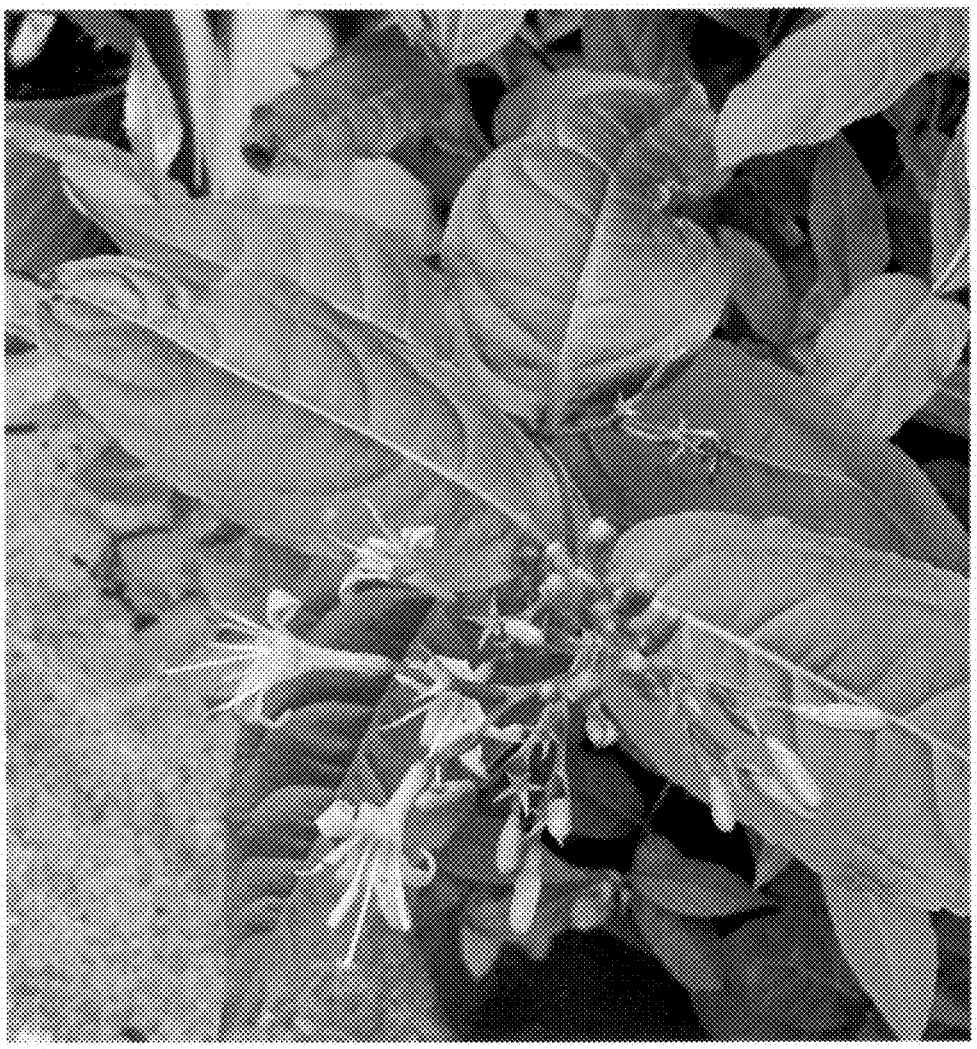

The photograph in FIG. 2 is a close-up view of an inflorescence of 'Baildierone'.

Figure 3:
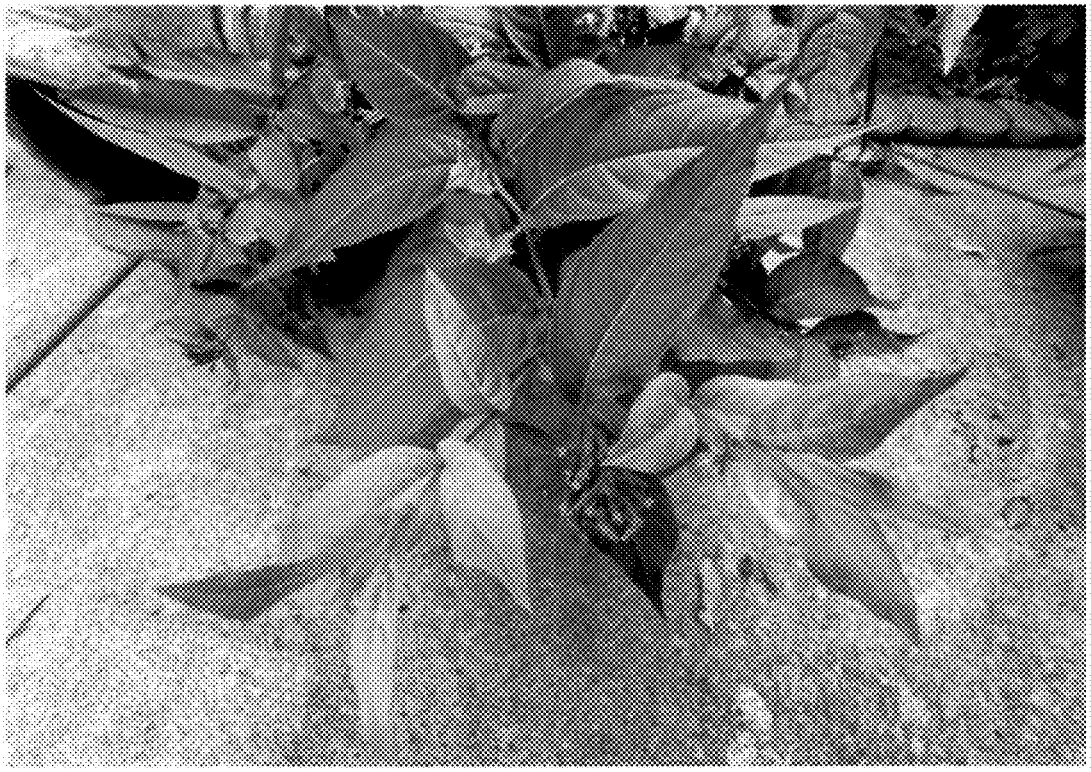

The photograph of FIG. 3 is a close-up view of the foliage with new growth.

Figure 4:
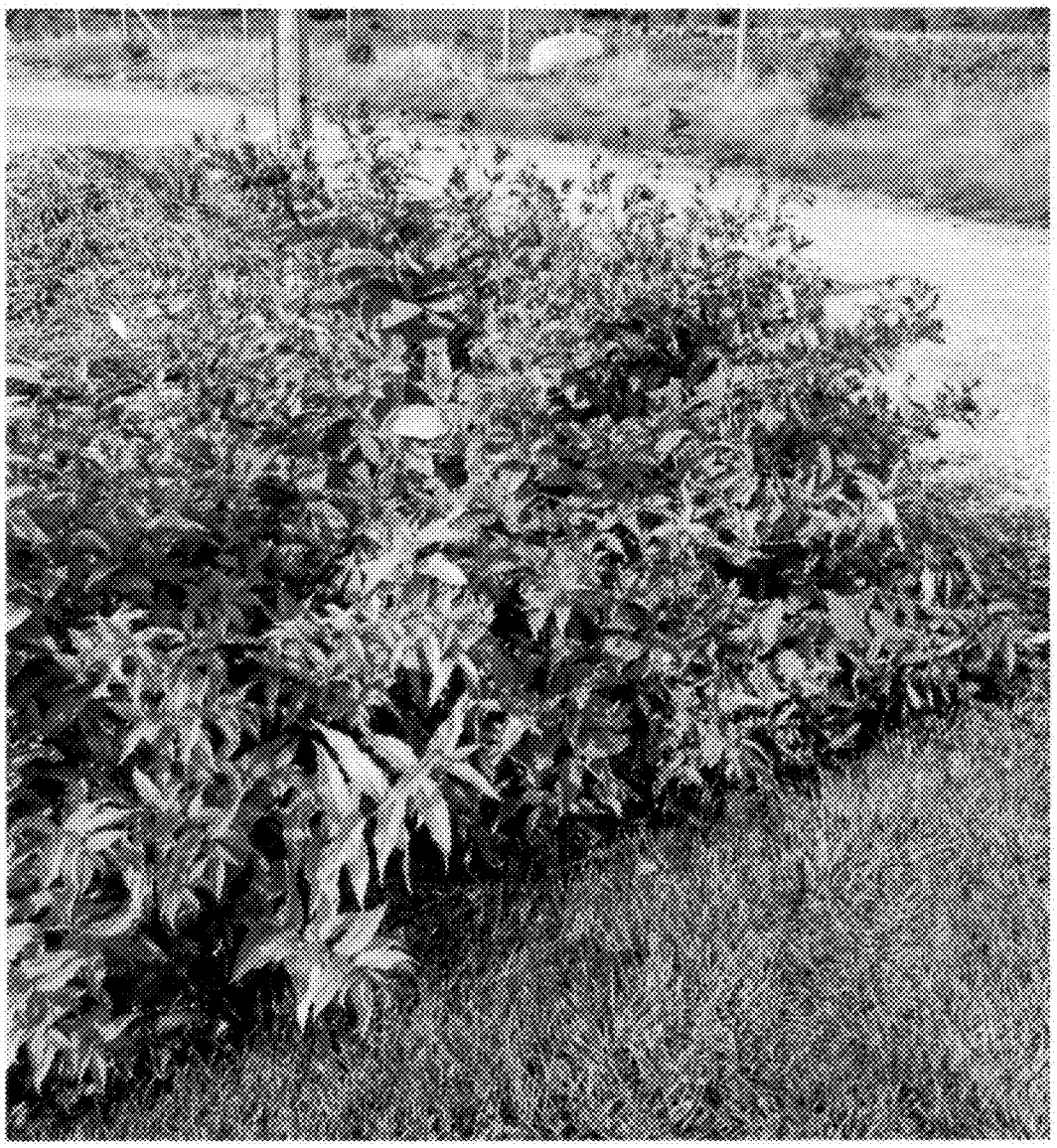

The photograph in FIG. 4 is a view of the fall foliage of 'Baildierone'.

The colors in the photographs are as close as possible with the digital photography techniques available, the color values cited in the detailed botanical description accurately describe the colors of the new *Diervilla*.

DETAILED BOTANICAL DESCRIPTION

The following is a detailed description of one year-old plants of the new cultivar as grown outdoors in a 2-gallon container in June in Newport, Minnesota. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms from June and repeats in late summer to September in Newport, Minnesota.

*Plant habit*.—Compact, dense, upright and spreading.

*Plant type*.—Perennial, deciduous shrub.

*Height and spread*.—Average of 1.2 m in height and spread in the landscape.

*Cold hardiness*.—At least in U.S.D.A. Zone 3.

*Diseases and pests*.—No susceptibility or resistance to diseases or pests has been observed.

*Propagation*.—Softwood stem cuttings.

*Root description*.—Fibrous, 161B in color.

*Root development*.—Roots initiate in 25 days and fully develop as a young rooted plant in 45 days.

*Growth rate*.—Moderate.

Branch description:

*Branch shape*.—Quadangular.

*Branch color*.—Young; 144B, then becoming flushed with 180A, mature; 175A.

*Branch size*.—An average of 45 cm in length and 4 cm in diameter.

*Branch surface*.—Young; slightly glossy, moderately covered with soft pubescent hairs that match surface color, mature; moderately to densely covered with soft pubescent hairs that range between matching the surface color and NN155D in color.

*Branch aspect*.—Held upright to slightly outward with a whorled appearance.

*Branch strength*.—Young; strong and bendable, mature; strong.

*Internode length*.—Average of 4 cm.

*Branching*.—An average of 30 branches emerging from base.

Foliage description:

*Leaf shape*.—Lanceolate.

*Leaf division*.—Simple.

*Leaf base*.—Truncate.

*Leaf apex*.—Apiculate.

*Leaf venation*.—Pinnate, upper and lower surfaces match leaf surface.

*Leaf margins*.—Serrate.

*Leaf arrangement*.—Opposite.

*Leaf attachment*.—Petiolate.

*Leaf surface*.—Upper surface; rugose, glabrous and matte, lower surface; rugose, glabrous and sheen, main vein is raised, glabrous, and glossy.

*Leaf size*.—Average of 9 cm in length and 3.5 cm in width.

*Leaf quantity*.—Average of 18 leaves per branch.

*Leaf color*.—Young upper and lower surface; spring and summer 145A, flushed with 174A, mature upper surface; spring and summer 138A and 145D, turning to a blend of 181A and 183A in fall, mature lower surface; 139D, turning to 183A in fall.

*Petioles*.—Average of 4 mm in length, 2 mm in width, both surfaces are matte and pubescent, color; 176A and 144A.

*Stipules*.—None present.

Inflorescence description:

*Inflorescence type*.—Terminal and axillary compound cymes of tubular flowers.

*Inflorescence size*.—Average of 3 cm in height and 4 cm in width.

*Flower fragrance*.—None.

*Lastingness of inflorescence*.—Average of one week, self-cleaning.

*Flower quantity*.—Average of 30 flowers stem, 12 per inflorescence.

*Flower type*.—Single, campanulate with tubular base.

*Flower size*.—Average of 1.7 cm in depth and 1.2 cm in diameter.

*Flower aspect*.—Upright to outward, en masse whorled.

*Flower buds*.—Narrow oblong in shape, 145A in color, glossy and glabrous surfaces.

*Peduncles*.—1.5 cm in length and 1 mm in diameter, strong, 144C in color, changing to 200A in color in fall, surface texture glabrous, round in shape.

*Pedicels*.—3 mm in length and 0.8 mm in diameter, moderately strong, 144C in color, changing to 200A in color in fall, glabrous surface, round in shape.

*Calyx*.—Rotate in shape, average of 2.5 mm in length and 2 mm in diameter, glabrous surface.

*Sepals*.—5, lanceolate in shape, narrow acuminate apex, base fused and cuneate, glabrous and matte on both surfaces, entire margin, average of 2 mm in length and 0.5 mm in width, color of both surfaces 144C.

*Petals*.—5, rotate with 5 lobes with lower 60% of petal fused into tube making a campanulate shape, both surfaces are glabrous, matte and slightly rugose, the lower lobe moderately covered with soft short hairs, 0.5 mm in length, NN155D in color, lobes; linear in shape, margins are entire and slightly undulate, rounded apex, average of 5 mm in length and 2 mm in width, color: upper surface when opening and fully open; 144B, lower lobe 149A, lower surface when opening and fully open; 144B, lower lobe 144B, as it matures and matures at fading to 178A, tube; average of 8 mm in length and 3 mm in width, 144C in color, surface is matte and glabrous.

Reproductive organs:

*Gynoecium*.—Pistil; 1, style; 1.7 cm in length and 149D in color, stigma; 0.5 mm in diameter, club-shape, 144A in color, ovary; 146D in color.

*Androecium*.—Stamens; 5, filaments; 145C in color and 6 mm in length, anthers; 4 mm in length and 164B in color, dorsifixed, pollen was not observed.

*Fruit and seed*.—No fruit or seed has been observed to date.

It is claimed:

1. A new and distinct cultivar of *Diervilla* plant named 'Baildierone' as herein illustrated and described.

* * * * *